United States Patent [19]

Billeter et al.

[11] Patent Number: 4,731,054
[45] Date of Patent: Mar. 15, 1988

[54] MEDICAL REPOSITORY PROBE

[75] Inventors: Werner Billeter, Winterthur; Peter Bittmann, Herrliberg, both of Switzerland

[73] Assignee: Sulzer Brothers Limited, Winterthur, Switzerland

[21] Appl. No.: 877,228

[22] Filed: Jun. 20, 1986

[30] Foreign Application Priority Data

Jul. 2, 1985 [CH] Switzerland ............... 2826/85

[51] Int. Cl.$^4$ ................................ A61M 11/00
[52] U.S. Cl. ........................... 604/93; 604/57; 604/265; 604/280
[58] Field of Search ............. 604/93, 57, 84, 890, 604/891, 265, 280, 289

[56] References Cited

U.S. PATENT DOCUMENTS

| | | | |
|---|---|---|---|
| 2,153,889 | 4/1939 | Hames | 604/891 |
| 2,473,363 | 6/1949 | Flintermann | 604/57 |
| 2,517,513 | 8/1950 | Vaernet | 604/891 |
| 4,326,522 | 4/1982 | Guerrero et al. | 604/57 |
| 4,578,263 | 3/1986 | Whitehead | 604/890 |

Primary Examiner—Stephen C. Pellegrino
Assistant Examiner—Gene B. Kartchner
Attorney, Agent, or Firm—Kenyon & Kenyon

[57] ABSTRACT

The repository probe or drug dispenser consists of a tube which is divided into a probe head and a probe end part. In addition, a series of medicine carriers are disposed in the probe head which contain active ingredients and which have an axial length of at most three times the outside diameter of the tube. In addition, openings are provided in the tube transversely of each medicine carrier for the passage of fluids. Joint zones are provided between the segments of the tube in which the medicine carriers are placed. Because of the limitation on the axial length of the medicine carriers and the joint zones, the flexibility of the probe head between the relatively stiff medicine carriers is increased without distortion or a closing of the openings to the medicine carriers when deflecting the probe.

19 Claims, 4 Drawing Figures

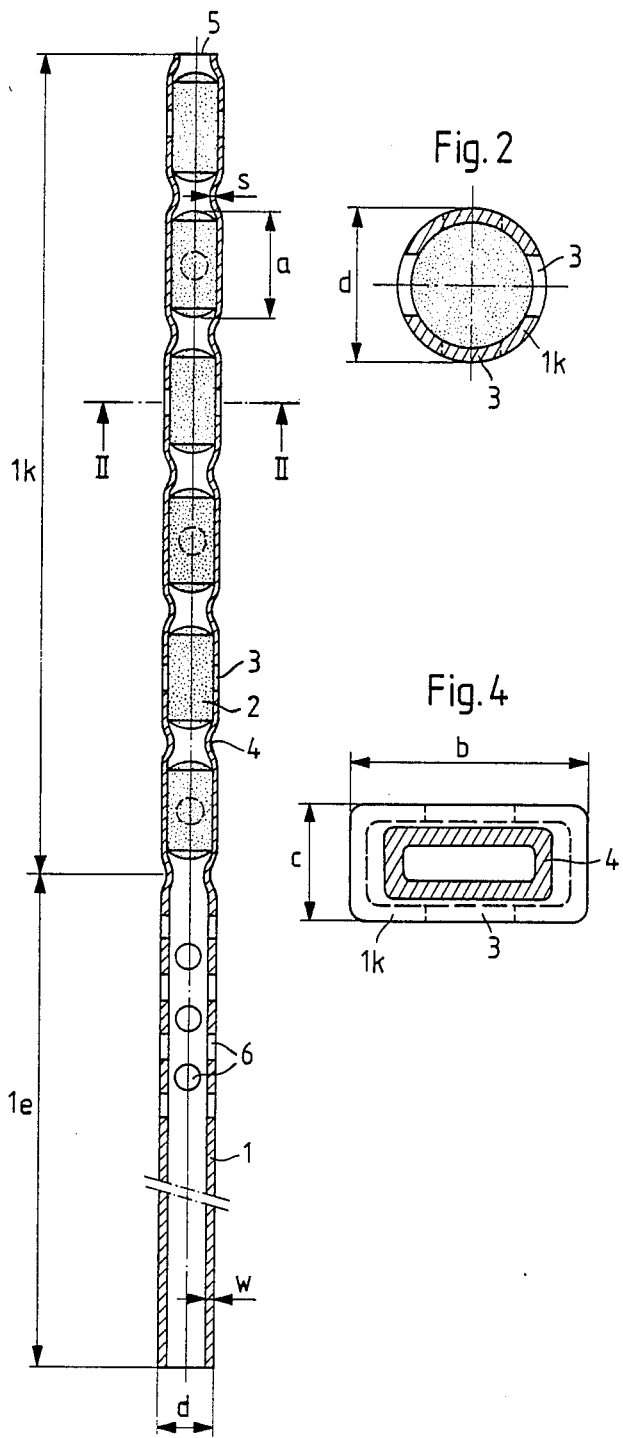
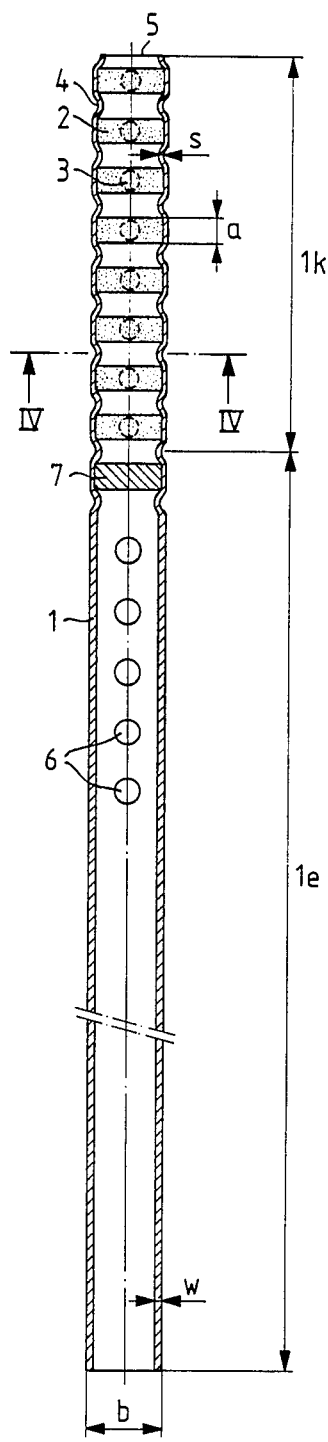

MEDICAL REPOSITORY PROBE

This invention relates to a medical repository probe.

As is known, various types of medical repository probes or implantale drug dispensers have been implanted in the human body in order to assure dispensation of a dosed amount of medicine over a certain period of time. For example German OS No. 3115763 describes a medical repository probe which can be implanted to dispense a medicine directly and locally, for example into the center of an infection. The probe is made of a non-porous smooth plastic and consists of a hollow probe head which contains a medicine carrier loaded with an active ingredient and a probe end part. Further, the probe head is divided into individual segments which are each filled with the medicine carrier and which are provided with a multiplicity of openings distributed over the probe head in the circumferential and axial direction. The openings permit body fluids to pass through in one direction while permitting the active ingredients to pass out in the other direction. In addition, solid elastic intermediate parts are provided between the segments which are penetrated, as are the segments, by an axial channel and a transverse channel in order to promote the drainage of secretions from the infected area. The connections between the segments or the probe end part, on the one hand, and the intermediate part, on the other hand, consist of adhesive, screw, plug or other connections which will not disconnect unintentionally.

As is known, medical repository probes should have a number of properties which are contradictory in part in order to be able to fulfill the desired function in an optimal manner. For example, the medical carriers must have at least a minimun strength so as not to crumble especially when inserted into muscle tissue or into places subjected to severe bending, in order to avoid having residual particles remain in the body after removal of the probe.

On the other hand, the probe head should be as flexible as possible so that the probe will not lead to mechanical irritations and so that the probe can be pushed with greater ease into an anatomically provided passages or canals.

Still another requirement voiced by physicians is that the wall thicknesses of the hollow part, especially in the probe head, should be as thin as possible in order to obtain the "flattest" possible through openings into which the least amount of tissue can grow. This is because this tissue is torn when the probe is removed. This, in turn leads to pain.

However, great flexibility of the probe head and relatively thin wall thicknesses can lead to severe deformations of the through openings when deflecting the probe. As a result, the openings can become much larger in the outer area of a bend where the hollow part is stretched while becoming smaller or even closed completely on the inside of the bend where the hollow part wall is compressed.

Accordingly, it is an object of the invention to provide a repository probe or drug dispenser with a highly flexible probe head in which distortions of the through openings are avoided to the greatest possible extent.

It is another object of the invention to provide a repository probe having relatively great flexibility and relatively thin wall thicknesses without adversely effecting the openings in the probe head.

Briefly, the invention provides a medical repository probe which is comprised of a tubular probe head having a plurality of individual mutually separated segments and a plurality of flexible joint zones disposed in alternating arrangement with the segments as well as a plurality of medicine carriers in the probe head which are disposed in the respective segments and which have an axial extent of at most three times the longest linear cross-section dimension of the probe head.

The relationship between the longest linear cross-section dimension of the probe head and the axial length of a medicine carrier necessitates relatively "short" medicine carriers disposed one after the other.

The repository probe may be formed of a single hollow flexible tube which defines the probe head as well as a probe end part. In this case, the joint zones are formed to advantage by constrictions of the hollow tube with the cross-sectional area of each constriction equal to from 35% to 70% of the undisturbed cross-sectional area of the probe head. Beyond this, due to the empty spaces of the constrictions, cavities are formed between the medicine carriers into which the probe wall-compressed at the inside radius of a curve when traversing a bent-can "escape".

Alternatively, the joint zones may be formed as bellows However, this would interfere with the smooth outside surface of the probe which is advantageous for as painless a removal of the probe as possible. In order to make the thinest possible wall thickness in the probe head, in the axial direction single opening is disposed only for each medicine carier. Preferably openings are circular in the undistorted state in order to obtain a high "tear resistance" when stressed in tension.

The size of the probe is determined primarily by the anatomical situation. Many infections to be treated locally occur in the extremeties of the body. In these cases, it is of great importance that the probe be capable of draining the secretions which develop post-operatively from the infected area. Where small probe diameters are involved, for example, five millimeters and smaller, it is impossible for purely design reasons, however, to accommodate the central lengthwise channel provided in the known probe without having to tolerate an intolerable reduction of the active ingredient charged in the probe head. Therefore, if the repository probe is to serve at the same time as a classical drainage hose, the probe end part and the probe head are made in one single hollow tube of a flexible material. Further, the probe end part area near the probe head is provided with drainage holes. With such a probe end part, the freed active ingredients always make direct contact with the tissue to be treated before being flushed out with the secretion flow, especially when the drainage is connected to a suction system In order to prevent a collapse of the drainage when applying a suction system, the wall thickness of the probe end part may be increased relative to that of the probe head which is determined solely by the tensile strength required. Alternatively, a collapse of the hollow probe end part can also be prevented by ribs which are disposed internally of the probe end part.

A partitioning wall may also be provided between the probe head and the probe end part in order to prevent that active ingredients which are dissolved in the secretion to be aspirated, will be drawn off dirrectly without contacts to the infected areas The tensile strength, particularly of the probe head can be improved by providing only two diametrically opposed openings trnsversely of each respective medicine carrier and by offsetting adjacent pairs of openings by 90°. A similar arrangement may also be used for the drainage holes in the probe end part.

These and other objects and advantages of the invention will become more apparent from the following detailed description taken in conjunction with the accompany drawings wherein:

FIG. 1 illustrates a longitudinal cross sectional view of a medical repository probe constructed in accordance with the invention;

FIG. 2 illustrates a view taken a line II—II of FIG. 1;

FIG. 3 illustrates a longitudinal cross sectional view of a modified medical repository probe in accordance with the invention; and FIG. 4 illustrates a view taken on line IV—IV of FIG. 3.

Referring to FIGS. 1 and 2, the medical repository probe is formed of a single hollow flexible tube 1 which defines a probe head $1k$ and a probe end part $1e$. As indicated the probe end part $1e$ has a greater wall thickness w than the thickness s of the probe head $1k$. Their absolute values depend on the "size" of the probe, that is, primarily on the diameter d of the tube 1. Further, this "size" depends on the medical application. For example, probes of larger outside diameter d are intended for use in the torso while probes for use in the extremities are of small diameter.

The hollow tube is made, for example of a softened PVC hose of medical quality which is commercially available. In order to shape the hose into the repository probe, the hose is subjected to a thermal treatment as is known for such plastics.

As shown in FIG. 1, the probe head has a plurality of individual mutually separated segments and a plurality of medicine carriers 2 each of which is disposed in a respective segment. These medicine carriers 2 are arranged in a single row axially one after another and each consists of waxy substances absolutely insoluble in water and having melting points between 60° and 100° C. By way of example, the substances are fatty alcohols such as hexadecanol, octadecanol, eiconsanol-or ester waxes on montan wax basis, such as "Hochst-Wachs E Pharma" of the Hochst Company. The medicine carriers 2 are loaded with active ingredients consisting of a water-soluble antibiotic or a water-soluble disinfectant, both of which must be suited for local application. Examples of the first class of active ingredients are amino glykosides (gentamicin, tobramicin, amicacin), polypeptide antibiotics (tyrothricin, bacitracin) or nitrofurances, and of the second class PVP iodine and other iodophorous polymers and biguanidines.

Each medical carrier 2 is of an axial extent of at most three times, and preferrably two times, the longest linear cross-section dimension of the probe head, i.e. the diameter d.

The tube of the probe is also provided with a plurality of openings 3 in the probe head $1a$. For example, a pair of diametrically opposed openings 3 are disposed transversely of each respective medicine carrier 2 and, provided the absolute dimensions of the tube 1 permit, each pair of openings 3 is offset by 90° relative to an adjacent pair of openings 3. This arrangement provides the advantage that not only two shell 27 areas are weakened in tensile strength throughout the axial length. The openings 3 may be stamped out of the tube 1 or may be formed in any other suitable manner. Further, the cross sectional areas of the openings 3 are selected to be as large as possible. The feature limiting the size of the openings is that the tube 1 must have a tensile strength sufficient to permit pulling of the probe out of the body after the release of the active ingredients. As indicated in FIG. 1, the probe head $1k$ has a plurality of joint zones 4 disposed in alternating arrangement with the segments containing the medical carriers 2. These joint zones consist of constrictions in the tube 1 and may be produced by a thermal treatment of the tube 1 with the aid of a core mould. In their linear dimensions, i.e. the diameter d, the constrictions are reduced to about 60% to 80% of their undisturbed dimensions. This, in turn, results in reductions of the cross-sectional areas of the constrictions to about 35% to 70% of the unisturbed cross section.

As indicated in FIG. 1, an opening 5 is formed at the terminal end of the probe head $1k$ and drainage hole S/6 are stamped out in the probe end part $1e$ near the probe head $1k$, for example, adjacent to the innermost constriction 4. If possible, the drainage hole S/6 are also offset mutually by 90° in an alternating manner.

Referring to FIGS. 3 and 4 wherein like reference characters indicate like parts as above, the tube 1 may have a rectangular cross-sectional shape. Such a shape is particularly useful in the extremities, for example in the fingers and toes as the probe is relatively flat. In this case, the constrictions 4 have linear dimensions relative to the side lengths b, c (see FIG. 4) such that the constrictions are reduced to about 60% to 80% of the undisturbed dimensions, resulting in reductions in the cross sectional areas to about 35% to 70% of the undisturbed cross section.

The drainage of secretions from the probe can be promoted by attaching the free end of the probe end part $1e$ to a suction system (not shown). In that case, a partitioning wall 7 as shown in FIG. 3 may be provided between the probe head $1k$ and the probe end part $1e$ in order to prevent direct aspiration of the active ingredients from the innermost medicine carrier 2. In the simplest case, this partitioning wall 7 may consist of a medicine carrier 2 which is not loaded with active ingredients.

In addition, a plurality of ribs (not shown) may be provided over the length of the probe end part $1e$ in order to support the hollow shape. These ribs serve to prevent a collapse of the probe end part $1e$ when applying the vacuum of a suction system.

By way of an example of each embodiment, reference is made to the following table.

|  | FIGS. 1 and 2 | FIGS. 3 and 4 |
| --- | --- | --- |
| Field of application | Torso | Fingers and Toes |
| Probe section (1k) | circular | rectangular |
| Dimensions in millimeters (mm) | | |
| overall length | 400 | 250 |
| probe head length | 60 | 45 |
| outside dimensions | 6 | 4 × 2 |
| wall thickness of probe head | 0.5 | 0.3 |
| wall thickness of probe end part | 0.75 | 0.6 |
| Through and drainage holes (3,6) | | |
| shape | circular | circular |
| diameter (millimeters) | 2 | 1.5 |
| Medicine Carrier (2) | | |
| number | 6 | 8 |
| shape | cylindrical | cuboidal |
| axial length (millimeters) | 6.5 | 3 |
| diameter or thickness (millimeters) | 5 | 1.4 |
| material | fatty alcohol | |

|  | FIGS. 1 and 2 | FIGS. 3 and 4 |
| --- | --- | --- |
| active ingredients | amino glykoside | iodine preparation |

The invention thus provides a medical repository probe which has relatively great flexibility due to the flexible joint zones 4 between the medical carriers 2. In addition, the medicine carriers 2 may have a strength sufficient so as to prevent crumbling, particularly when subjected to bending of the probe. Still further, the wall thicknesses of the probe may be as thin as possible in order to obtain the flattest possible opening through which a minimum amount tissue may grow. In this way, pain may be avoided when the probe is removed from the patient.

Since the openings are provided in the same plane as the medicine carriers, and since flexing takes part at the joints 4, the openings do not deform when the probe is deflected. Thus, when implanted, the medicine can be dosed in the proper amounts over a certain period of time.

Because of the limited axial length of the medicine carriers relative to the tube of the probe, and because of the joint zones between the medicine carriers, the flexibility of the probe head is increased between the relatively stiff medicine carriers without the occurrence of distortions or of a closing of the transverse openings when the probe is deflected.

What is claimed is:

1. A medical repository probe comprising
   a tubular probe head having a plurality of individual mutually separated segments and a plurality of flexible joint zones disposed in alternating arrangement with said segments;
   a plurality of medicine carriers in said probe head, each said carrier being disposed in a respective segment and having an axial extent of at most three times the longest linear cross-sectional dimensions of said probe head; and
   a tubular probe end part extending from said probe head.

2. A medical repository probe a set forth in claim 1 wherein said probe head has constrictions forming said joint zones.

3. A medical respository probe as set forth in claim 2 wherein said constrictions have a cross-sectional area equal to from 35% to 70% of the undisturbed cross-sectional area of said probe head.

4. A medical repository probe as set forth in claim 1 which further includes a plurality of openings in said probe head, each said opening being disposed transversely of a respective carrier.

5. A medical repository probe comprising
   a tubular probe head having a plurality of individual mutually separated segments and a plurality of flexible joint zones disposed in alternating arrangement with said segments;
   a tubular probe end part extending from said probe head to define a single tube, said tube being made of flexible material; and
   a plurality of medicine carriers in said probe head, each said carrier being disposed in a respective segment and having an axial extent of at most three times the longest linear cross-section dimension of said probe head.

6. A medical repository probe as set forth in claim 5 which further includes a plurality of pairs of diametrically opposed openings in said probe head, each said pair of openings being disposed transversely of a respective carrier and offset 90° relative to an adjacent pair of openings.

7. A medical repository probe as set forth in claim 5 wherein said probe end part has a greater wall thickness than said probe head.

8. A medical repository probe as set forth in claim 5 which further includes a plurality of drainage holes in said probe end part near said probe head.

9. A medical repository probe as set forth in claim 8 which further comprises a partition between said probe head and said probe end part.

10. A medical repository probe as set forth in claim 5 which further comprises a plurality of ribs internally within and on said probe end part to stiffen said part against collapsing 11. A medical repository probe comprising
    a hollow flexible tube defining a probe head and a probe end part, said tube having a plurality of alternating segments and joint zones in said probe head; and
    a plurality of medicine carriers in said probe head, each said carrier being disposed in a respective segment and having an axial extent of at most three times the longest linear cross-sectional dimension of said tube.

12. A medical repository probe as set forth in claim 11 wherein said tube is cylindrical.

13. A medical repository probe as set forth in claim 11 wherein said tube has a rectangular cross-sectional shape.

14. A medical repository probe as set forth in claim 11 wherein said joint zones have a cross-sectional area equal to form 35% to 70% of the undisturbed cross-sectional area of said probe head.

15. A medical repository probe as set forth in claim 11 which further includes a plurality of pairs of diametrically opposed openings in said probe head, each said pair of openings being disposed transversely of a respective carrier.

16. A medical repository probe as set forth in claim 15 which further includes a plurality of drainage holes in said probe end part near said probe head.

17. A medical repository probe as set forth in claim 11 wherein said probe end part has a greater wall thickness than said probe head and a plurality of openings for dispensing of medicine from said carriers therein.

18. A medical repository probe as set forth in claim 11 wherein said probe end part and said segments of said probe head have equal cross-sectional shape and wherein said probe end part has a greater wall thickness than said segments of said probe head.

19. A medical repository probe comprising
    a tubular probe head having a plurality of individual mutually separated segments and a plurality of flexible joint zones disposed in alternating arrangement with said segments and a tubular probe end part extending coaxially from said probe head and being of greater wall thickness than said probe head; and
    a plurality of medicine carriers in said probe head, each said carrier being disposed in a respective segment and having an axial extent of at most three times the longest linear cross-section dimension of said probe head.

* * * * *

UNITED STATES PATENT AND TRADEMARK OFFICE
CERTIFICATE OF CORRECTION

PATENT NO. : 4,731,054

DATED : March 15, 1988

INVENTOR(S) : Werner Billeter, et al

It is certified that error appears in the above-identified patent and that said Letters Patent is hereby corrected as shown below:

```
Column 1, line 6  "implantale" should be -implantable-
Column 1, line 7  "assure dispensa-" should be -assure the
     dispensa- -
Column 1, line 36 "minimun" should be -minimum-
Column 2, line 30 "direction single" should be -direction a
     single-
Column 2, line 31 "carier" should be -carrier-
Column 2, line 65 "dirrectly" should be -directly-
Column 3, line 21 "indicated the" should be -indicated, the-
Column 3, line 45 "with. active" should be -with active-
Column 3, line 64 "shell 27" should be -shell-
Column 4, line 14 "unisturbed" should be -undisturbed-
Column 4, line 20 "hole S/6" should be -holes 6-
Column 5, line 10 "medical" should be -medicine-
Column 5, line 16 "amount tissue" should be -amount of tissue-
Column 5, line 20 "takes part" should be -takes place-
Column 5, line 45 "a" should be -as-
Column 6, line 36 "form" should be -from-
```

Signed and Sealed this

Twenty-seventh Day of September, 1988

Attest:

DONALD J. QUIGG

*Attesting Officer*  *Commissioner of Patents and Trademarks*